(12) United States Patent
Geracioti, Jr. et al.

(10) Patent No.: US 6,359,010 B1
(45) Date of Patent: Mar. 19, 2002

(54) METHODS OF TREATING ANXIETY AND MOOD DISORDERS WITH OLEAMIDE

(76) Inventors: Thomas D. Geracioti, Jr., 254 Greendale Ave., Cincinnati, OH (US) 45220; John W. Kasckow, 9202 Sheralce La., Cincinnati, OH (US) 45231

( * ) Notice: Subject to any disclaimer, the term of this patent is extended or adjusted under 35 U.S.C. 154(b) by 0 days.

(21) Appl. No.: 09/718,639

(22) Filed: Nov. 22, 2000

Related U.S. Application Data

(60) Provisional application No. 60/167,183, filed on Nov. 23, 1999.

(51) Int. Cl.⁷ .............................................. A61K 31/16
(52) U.S. Cl. ...................................... 514/627; 514/625
(58) Field of Search .................................. 514/627, 625

(56) References Cited

PUBLICATIONS

Arato M. Banki CM, Bissette G, Nemeroff CB, Elevated CSF CRH in suicide victims. Biological Psychiatry 1989;25:355–359.

Baker DG, West SA, Nicholson WE, Ekhator NN, Kasckow JW, Hill KK, Bruce AB, Orth DN, Geracioti TD Jr. Serial CSF corticotropin–releasing hormone levels and adrenocortical activity in combat veterans with post–traumatic stress disorder. Am J Psychiatry 1999;156:585–588.

Banki CM, Bissette G, Arato M, O'Connor L, Nemeroff CB. Cerebrospinal fluid corticotropin releasing factor–like immunoreactivity in depression and schizophrenia. Am J Psychiatry 1987; 144:873–877.

Basile AS, Hanus L, Mendelson WB. Characterization of the hypnotic properties of oleamide. Neuroreport 1999;10:947–951.

Brady LS, Whitfield HJ Jr., Fox RJ, Gold PW, Herkenham M. Long–term antidepressant administration alters corticotropin–releasing hormone, tyrosine hydroxylase, and mineralocorticoid receptor gene expression in rat brain. Therapeutic implications. J Clin Invest 1991;87:831–837.

Brady LS, Gold PW, Herkenham M, Lynn AB, Whitfield HJ Jr. The antidepressants fluoxetine, idazoxan and phenelzine alter corticotropin–releasing hormone and tyrosine hydroxylase mRNA levels in rat brain: therapeutic implications. Brain Res 1992;527:117–125.

Brady LS, Lynn AB, Glowa JR, Le DQ, Herkenham M. Repeated electroconvulsive shock produces long–lasting increases in messenger RNA expression of corticotropin–releasing hormone and tyrosine hydroxylase in rat brain. Therapeutic implications. J Clin Invest 1994;94:1263–1268.

Casper RC, Kocsis J, Dysken M, Stokes P, Croughan J, Maas J. Cortisol measures in primary major depressive disorder with hypersomnia or appetite increase. J Affect Disord 1988;15:131–140.

Cheer JF, Cadogan A–K, Marsden CA, Fone KCF, Kendall DA. Modification of 5–HT2 receptor mediated behavior in the rat by oleamide and the role of cannabinoid receptors. Neuropharmacol 1999;38:533–541.

Cravatt BF, Prospero–Garcia O, Siuzdak G, Gilula NB, Henriksen SJ, Boger DL, Lerner RA. Chemical characterization of a family of brain lipids that induce sleep. Science 1995;268:1506–1509.

Cravatt BF. Giang DK, Mayfield SP, Boger DL, Lerner RA, Gilula NB. Molecular characterization of an enzyme that degrades neuromodulatory fatty–acid amides. Nature 1996;384:83–87.

Geracioti TD Jr, Orth DN, Ekhator NN, Blumenkopf B, Loosen PT. Serial cerebrospinal fluid corticotropin–releasing hormone concentrations in healthy and depressed humans. J Clin Endocrinol Metab 1992;74:1325–1330.

Geracioti TD Jr, Loosen PT, Orth DN. Low cerebrospinal fluid corticotropin–releasing hormone concentrations in eucortisolemic depression. Biological Psychiatry 1997;42:166–174.

Gold PW, Goodwin FK, Chrousos GP. Clinical biochemical manifestations of depression: Relation to the neurobiology of stress (part II of parts). N Engl. Med 1988;319:413–420.

Huidobro–Toro JP, Harris RA. Brain lipids that induce sleep are novel modulators of 5–hydroxytryptaine receptors. Proc Natl Acad Sci USA 1996;93:8078–8082.

Kasckow JW, Regmi Gill PS, Parkes DG, Geracioti TD. Regulation of corticotropin–releasing factor (CRF) messenger RNA and CRF peptide in the amygdala: studies in primary amygdalar cultures Endocrinology 1997;138:4774–4792.

Lerner RA, Siuzdak G, Prospero–Garcia O, Henriksen SJ, Boger DL, Cravatt BF. Proc Natl Acad Sci USA 1994;91:9505–9508.

Lister RG. The use of a plus maze to measure anxiety in the mouse. Psychopharmacology 92: 180–185, 1987.

Mulchahey JJ, Regmi A. Sheriff S. Balasubramanian A, Kasckow JW. Coordinate and divergent regulation of corticotropin–releasing factor (CRF) and CRF–binding protein expression in an immortalized amygdalar neuronal cell line. Endocrinology 1999;140: 251–259.

Nemeroff, C.B., Widerlov E, Bissette G, et al., Elevated concentrations of CSF corticotropin–releasing factor–like immunoreactivity in depressed patients. Science 1984;226:1342–1344.

Sachar EJ. Corticosteriods in depressive illness: II. A longitudinal psychoendocrine study. Arch Gen Psychiatry 1967;17:554–567.

(List continued on next page.)

*Primary Examiner*—William R. A. Jarvis
(74) *Attorney, Agent, or Firm*—Frost Brown Todd LLC

(57) ABSTRACT

A method of treating conditions characterized by anxiety and/or depression, by the administration of oleamide or related compounds is disclosed.

13 Claims, 2 Drawing Sheets

PUBLICATIONS

Sladek TL, Jacobberger JW, 1992, Simian virus 40 large T-antigen expression decreases the G1 and increases the G2+M cell cycle phase durations in exponentially growing cells. J Virology 66: 1059–1065.

Thomas, E.A., Cravatt BF, Sutcliffe JG. The endogenous lipid oleamide activates serotonin 5-HT7 neurons in mouse thalamus and hypothalamus. J Neurochem 1999;72:2370–2378.

Windle RJ, Shanks N, Lightman SL, Ingram CD. Central oxytocin administration reduces stress-induced corticosterone release and anxiety behavior in rats. Endocrinology 138: 2829–2834, 1997.

METHODS OF TREATING ANXIETY AND MOOD DISORDERS WITH OLEAMIDE

This application is based on and claims priority from U.S. Provisional Patent Application No. 60/167,183, Geracioti and Kasckow, filed Nov. 23, 1999.

All or part of this work was performed during the course of the inventors' employment by the U.S. Government. Accordingly, the U.S. Government may have certain rights with regard to the invention.

BACKGROUND OF THE INVENTION

The mood and anxiety disorders in their various permutations constitute a major source of personal suffering and impaired ability to engage in productive work and interpersonal relationships. Between 5 and 9% of women and between 2 and 3% of men meet the diagnostic criteria for major depression at any time; 10–25% of all women suffer major depression sometime in their lives, while 5–10% of men will develop major depressive disorder (American Psychiatric Association, 1994). The anxiety disorders obsessive-compulsive disorder (OCD), post-traumatic stress disorder (PTSD), panic disorder, and generalized anxiety disorder (GAD) show lifetime prevalence rates of approximately 2.5%, 7%, 2.5%, and 5% respectively. Between 3 and 13% of individuals in community samples are regarded to meet the diagnostic criteria for social phobia. Mood and anxiety disorders are common comorbidities (American Psychiatric Association, 1994) and the most common antidepressant medications—including the serotonin reuptake inhibitors, the mixed serotonin-catecholamine reuptake inhibitors, the tricyclic antidepressants, and the monoamine oxidase inhibitors—are all effective treatments for anxiety and panic attacks.

Affective disorders, while characterized by depressed mood of varying degrees, exist in various forms. Thus, melancholic depression is characterized by continuously-depressed mood and pervasive hopelessness, insomnia with early-morning awakening (with the inability to return to sleep), loss of appetite and weight loss, and excessive feelings of guilt (American Psychiatric Association, 1994). In contrast, so-called "atypical" depression is characterized by hypersomnia (oversleeping), hyperphagia and weight gain, and—often—mood reactivity. In general—regardless of whether or not the depressive syndrome is melancholic, atypical, or some admixture of the two—a diagnosis of major depression is given when depressed mood is present, or loss of interest or pleasure in all activities is present, for at least two weeks (American Psychiatric Association 1994). If less severe or incapacitating, depressed mood is considered dysthymia. Depressed mood can occur in the form of a cycling mood abnormality such as bipolar mood disorder, cyclothymia, or menstrual-related mood disorder.

Mood disorders are commonly seen in general medical practice and some general medical disorders resemble depression in important respects. In particular, both fibromyalgia and chronic fatigue syndrome are medical disorders that have clinical and pathophysiologic features in common with atypical depression.

It is widely accepted that the hypothalamic-pituitary-adrenocortical axis is dysregulated in patients with major depression. One of the early findings of biological psychiatry was that approximately 50% of depressed patients showed hypercortisolemia—increased concentrations of the circulating steroid cortisol, produced by the adrenal cortex (Sachar 1967). This led to the hypothesis that the principle central nervous system (CNS) effector of the HPA axis, corticotropin-releasing hormone (CRH), was hypersecreted in depressed patients. Elevated levels of CRH in the cerebrospinal fluid (CSF) of depressed patients were subsequently observed, consistent with this hypothesis (Nemeroff et al 1984, Banki et al 1987, Arato et al 1989). Similarly, some patients with anxiety disorders—such as post-traumatic stress syndrome—have elevated CSF levels of CRH (Baker et al 1999). However, it has also become appreciated that many depressed patients, with or without anxiety disorders, do not show hypercortisolemia and, in fact, show evidence of an insufficient or pathologically inactive hypothalamic-pituitary-adrenocortical axis (Casper et al., 1988, Vanderpool et al., 1991). These patients, most often the atypically depressed or eucortisolemic, have low CSF CRH levels (Geracioti et al., 1992 & 1997). Evidence of low CRH activity has also been found in patients with chronic fatigue syndrome and fibromyalgia (Demitrack and Crofford 1998).

Mood and anxiety disorders very frequently coexist in the same individual. In this regard, it is now appreciated that almost all antidepressants improve anxiety symptoms. Conversely, the most popular anxiolytics, the benzodiazepines, improve mood acutely but are typically ineffective or harmful to mood during chronic use.

The current psychopharmacologic treatments of affective and anxiety disorders are limited. A significant portion of depressed patients are resistant to treatment with existing antidepressants or combinations thereof either because of non-responsiveness or because a positive effect wears off (breakthrough depression) or is inadequate (depression in partial remission). Troubling side effects may also be seen with existing antidepressants. After beginning daily administration, psychopharmacologic anti-depressants at present have a latency of typically two weeks before the onset of significant antidepressant activity. As noted, antidepressant drugs are also used to treat anxiety disorders; the limitations of these drugs in treating anxiety are similar to those faced in attempts to treat depression: many patients are resistant to treatment or gain only partial or short-lasting responses; the common side effects are troubling (for example, the serotonin-reuptake inhibitors are the drugs most commonly used to treat unipolar depression and the most commonly-used agents to treat obsessive-compulsive disorder; these agents may have significant, unwanted sexual and/or gastrointestinal side effects in both male and female patients—among other side effects—and are either ineffective or only partially effective in a substantial percentage of patients). The most commonly used anxiolytic medications, the benzodiazepines, have a number of major limitations: (a) tolerance to their effects rapidly develops, with increasing doses becoming required to achieve the same effect; (b) benzodiazepine dependence is a standard occurrence after chronic use; (c) major withdrawal syndromes are seen—including grand mal seizures—after abrupt discontinuation; (d) overdose is associated with respiratory depression and sometimes death; (e) effects are potentiated by alcohol, which is cross-tolerant with the benzodiazepines; and (f) high abuse potential.

SUMMARY OF THE INVENTION

In a series of in vitro and in vivo behavioral experiments we find that subhypnotic doses of oleamide have actions predictive of anti-anxiety and antidepressant effects. Our data also indicate that it has a rapid onset of action. Specifically, we found that oleamide acutely increases CRH messenger ribonucleic acid (mRNA) expression in explanted hypothalamic cell cultures in a concentration-dependent manner and also stimulates release of CRH from these cells. See FIGS. 1 and 2. This effect (increase in CRH mRNA in the hypothalamus) is also seen after electroconvulsive therapy (ECT) in rats (Brady et al 1994). ECT has potent antidepressant effects. In fact, the clinically-used antidepressant medications tested, such as the tricyclic antidepressants, the serotonin-reuptake inhibitors, and monoamine oxidase inhibitors, all modify brain CRH mRNA levels (Brady et al 1991 & 1992). Moreover, dysregulation of CNS CRH release is regarded to be of fundamental pathophysiologic significance in clinical depression (Gold et al 1988). Our behavioral findings support our in vitro observations about the antidepressant and anxiolytic effects of oleamide. Specifically, IP dosing of oleamide enhances exploratory behavior on the elevated plus maze in the context of decreasing overall activity.

The present invention relates to a method for treating mood and anxiety disorders in humans or animals in need of such treatment by administering a safe and effective dose of oleamide, an oleamide analog, an inhibitor of oleamide degradation or clearance, or an oleamide antagonist.

DETAILED DESCRIPTION OF THE INVENTION

Figure 1A:
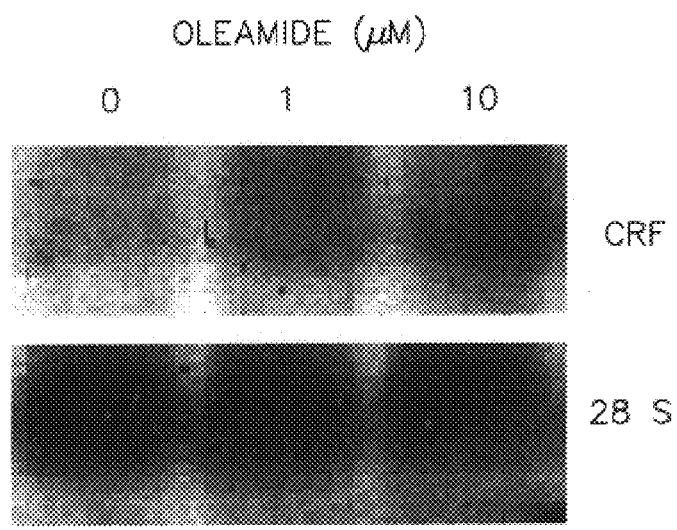
FIG. 1A represents computer-generated autoradiograms from the experimental portion of this application.

The present invention relates to the use of oleamide and related compounds to treat mood disorders (such as depression, major depression, melancholic depression, atypical depression, minor depression, seasonal depression, bipolar affective disorder, dysthymia, menstrual cycle-related dysphoria, chronic fatigue syndrome, depression associated with somatoform disorders, fibromyalgia and treatment-resistant depression) and anxiety disorders (such as post-traumatic stress disorder, generalized anxiety disorder, panic disorder with and without agoraphobia, social phobia, tics, tourette's syndrome, and obsessive-compulsive disorder). This treatment is accomplished by administering to the patient a safe and effective amount of oleamide, an oleamide analog, an inhibitor of oleamide degradation or clearance or an oleamide antagonist. Oleamide is the preferred compound for use in the present invention.

Oleamide

Unsaturated fatty acid amides represent a unique class of signaling molecules within the central nervous system (Lerner et al 1994, Cravatt et al 1995, Basile et al 1999). The fatty acid amides appear to be simple molecules with a great deal of diversity based on differing alkane chain lengths, stereochemistry, and locations of double bonds (Cravatt et al 1995).

Oleamide, a lipid originally named "cerebrodiene," was first isolated from partially sleep-deprived cats (Lerner et al 1994). The molecule, with the chemical formula $C_{18}H_{35}NO$, is a long-chain base structurally related to sphingosine and sphinganine (Lerner et al 1994). Oleamide, or cerebrodiene, is chemically characterized as cis-9,10-octadecenoamide (Cravatt et al 1995). Oleamide is degraded by the brain enzyme fatty acid amide hydrolase (FAAH), which also degrades anandamide (Cravatt et al, Nature 1996).

Synthetic cis-9,10-octadecenoamide induced 1–2.5 h of sleep in rats when injected intraperitoneally in doses between 5 and 50 mg (Cravatt et al 1995). Doses between 5 and 150 mg reduce sleep latency in rats while sleep-deprived rats develop two- to three-fold increases in CSF oleamide levels (Basile et al 1999).

Oleamide markedly potentiates 5-HT-elicited currents in oocytes expressing the rat 5-HT2 receptor, probably as an allosteric regulator, but has no significant direct effects (Huidobro-Tora & Harris 1996). The parent compound oleic acid does not have any effect, indicating the necessary presence of the amide group. A related fatty acid, octadecanamide had effects on the 5HT receptor that were opposite those of oleamide (Huidobro-Tora & Harris 1996). In vivo evidence also suggests that oleamide indirectly potentiates 5HT2 function (Cheer et al 1999). Oleamide had no significant effects on the ionotropic $GABA_A$, N-methyl-D-aspartate (NDMA), and 5HT3 receptors. The possibility that lipid amides modulate other G-protein-coupled receptors is of great interest.

Intra-perotineal (IP) administration of 5 or 10 mg/kg (but not 1 mg/kg) of oleamide to rodents resulted in activation of multiple brain areas, as judged by the transient induction of c-fos mRNA, including anterior cingulate and somatosensory cortex, lateral septum, hippocampal area CA1, and multiple thalamic and hypothalamic nuclei (Thomas et al 1999).

Oleamide analogs are also useful in the treatment methods of the present invention. Oleamide analogs include $C_{12}$–$C_{24}$ saturated and unsaturated fatty acid amides, with the saturated amides being preferred, and the saturated $C_{16}$–$C_{20}$ amides being particularly preferred. Since control of oleamide levels in the body is important to achieving the benefits described herein, inhibitors of oleamide degradation or clearance (such as the oleamide hydrolase inhibitors described in U.S. Pat. No. 5,856,537) and oleamide antagonists may also be used in the present invention.

The active ingredients may be administered by any conventional route, such as orally, transdermally, subcutaneously, parenterally, intramuscularly, intravenously, intraperitoneally, or via inhalation. Oral, parenteral and subcutaneous administration are preferred. The active compounds may be administered alone or in combination with other therapies conventionally known for mood or anxiety disorders.

The active compounds are administered to the patient in a "safe and effective amount", i.e., an amount which provides the desired pharmacological benefit based on the size, weight, age, physical and mental condition of the patient, while minimizing any undesired side effects. The precise dosages to be administered will be determined based on the judgment of the treating physician. Typical dosages for administration of the active compounds would be from about 0.001 to about 150 mg/kg, more preferably from about 0.01 to about 15 mg/kg, on a daily basis. The active compounds may be combined with pharmaceutically-acceptable carriers and other conventional pharmaceutical adjunct materials and formulated into a variety of dosage forms.

The following experiments demonstrate the efficacy of the present invention.

Methods Used

Immortalization of Hypothalamic Cells

Embryonic day 19 Sprague Dawley rats were humanely dissected from pregnant rats and decapitated as described by Kasckow et al. (1997). The hypothalamus was removed and sliced. Hypothalamic slices were placed in phosphate buffered saline (PBS: NaCl, 137 mM; $Na_2HPO_4$, 21 mM; $KH_2PO_4$, 29 mM; KCl, 1.2 mM; pH 7.3). Cells were dissociated for 10–15 minutes in 0.25% trypsin containing 75 units/ml of DNAse in serum-free media (SFM) consisting of a mixture of Dulbecco's modified essential medium and Ham's F-12 (1:1, v/v from Gibco) supplemented with 14 mM glucose, 15 mM $NaHCO_3$, 5 mM Hepes and 0.05 U/ml of penicillin streptomycin (Sigma). Cells were collected by centrifugation (500 Xg, 5 min), resuspended in SFM supplemented with 7.5% fetal calf serum (Atlanta Biologicals) and plated as described by Kasckow et al (1997) at a density of 2 million cells per well using 6 well plates (Costar). Plates had been coated with gelatin (250 mg/ml, 30 min, room temperature[RT]) and polyornithine (MW=40,000, 1.5 mg/ml, overnight at RT) and cells were incubated at 37° C. in a 95% $O_2$/5% $CO_2$ atmosphere.

Virus producer cell line γCRE/pZIPTEX was propagated at $1\times10^6$ cells per 100 mm tissue culture dish in the same media used for dissociated hypothalamic cultures (SFM+ 7.5% fetal bovine serum). Infection of the primary culture was performed as described previously (Frisa et al., 1994; Sladek and Jacobberger, 1992) with modifications. Viral culture supernatant was mixed with polybrene (final concentration 4 µg/mL) and $2\times10^6$ amygdalar cells. This was incubated with gentle agitation for 6 hours at 37° C. At the time of infection, the virus producer line had been propagated for three days and the primary amygdalar cultures were three days post-dissociation. Thirty hours after infection, cells were treated with 0.8 µg/mL geneticin (G418, Sigma Chemicals, St. Louis, Mo.) and 5 days after this treatment, surviving colonies were cloned in 98 well tissue culture dishes. Wells containing single cells were propagated and replated in 6 well culture dishes. One cell was selected on the basis of CRH peptide production which was monitored by radioimmunoassay (described below). This is referred to as clone IVB.

Stimulation Experiments

For analysis of CRH mRNA, clone IVB cells were plated at a density of 2 million cells per well using 6 well plates (Costar). Cells were washed with serum free media and test substances in incubation medium (β-Pit Julip+0.1% BSA) were added based on Mulchahey et al (1999). Cultures were incubated with vehicle(1:1000 absolute ethanol in incubation media) or oleamide (diluted in the same vehicle).

CRH Messenger RNA (mRNA) Detection by Northern Hybridization

Total RNA was isolated using the PUREscript RNA isolation kit (Gentra Systems, Minneapolis, Minn.). Twenty mg total RNA per lane was electrophoresed in an acrylamide-formaldehyde gel (1.2%/2.2 M) for 2 hours at 80 volts as previously described (Sambrook et al 1989). RNA was transferred to a Hybond-N nylon membrane (Amersham) at 2° C. overnight at 0.25 mA. The membrane with the RNA was UV cross-linked using a Stratalinker 1800 apparatus (Stratagene, La Jolla, Calif.) and prehybridized in ExpressHyb hybridization solution (Clonetech, Palo Alto) for 30 minutes at 65° C. For CRH, a $^{32}P$-labelled DNA probe was generated containing the rat CRF exon II with a PrimeIt-II random oligonucleotide priming kit (Stratagene). The EcoR1/Hind III fragment was generated from a pGEM3Zbam761 construct. The membrane was then hybridized at 65° C. with $1\times10^6$ cpm/ml labeled probe in ExpressHyb hybridization solution for 1 hour. After washing, the membrane was exposed to Xomatic film (Kodak) for 24–48 hours and then developed. A Foto/Eclipse Imager (Fotodyne Inc., Hartland, Wis.) interfaced with Power Macintosh 8100/110 using NIH ImageQuant analysis software was utilized for densitometric quantitation of the mRNA bands.

Radioimmunoassay (RIA)

RIA for CRH was performed according to the protocol provided by IgG Corporation (Nashville, Tenn.) utilizing the reagents provided. For CRH RIA, rabbit anti-hCRH serum was diluted 1:100 in RIA buffer (63 mM $Na_2HPO_4$ $7H_2O$ [pH 7.4], 13 mM $Na_2EDTA$, 3 mM sodium azide, 0.1% Triton X-100 [v/v] and 250 KIU aprotinin) and incubated with tissue samples or supernatant for 3 days at 4° C. One hundred mL [$^{125}I$]-0Tyr-CRH (1000 cpm; Dupont-NEN) was then added and samples were incubated for two additional days at 4° C. Following this, goat anti-rabbit gamma globulin was added and after 4 hours at 4° C. samples were precipitated by centrifugation at 5000×g at 4° C. in RIA buffer containing 2.5% bovine serum albumin. Radioactivity of the pellet was measured using a Packard Multi-Prias 4 gamma counter (Packard Instruments, Downers, Ill.).

Statistical Analysis

The quantitative data obtained were expressed as mean±standard error. Data were subjected to ANOVA followed by Student's t test with the Bonferroni correction using INSTAT Software (Loyola University Medical Center, Chicago, Ill.). A P value less than 0.05 was considered sufficient to reject the null hypothesis.

Results

Figure 1B:
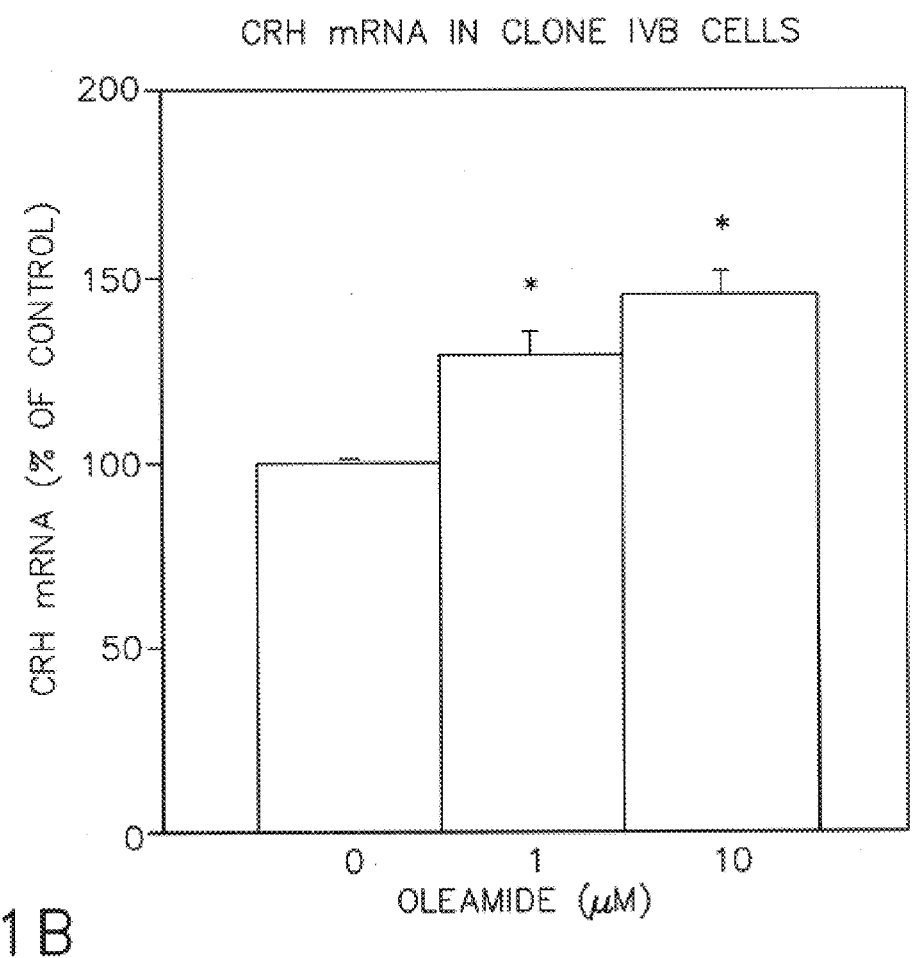
FIG. 1B is a plot of densitometric values of CRH mRNA levels from various levels of oleamide tested.
Figure 2:
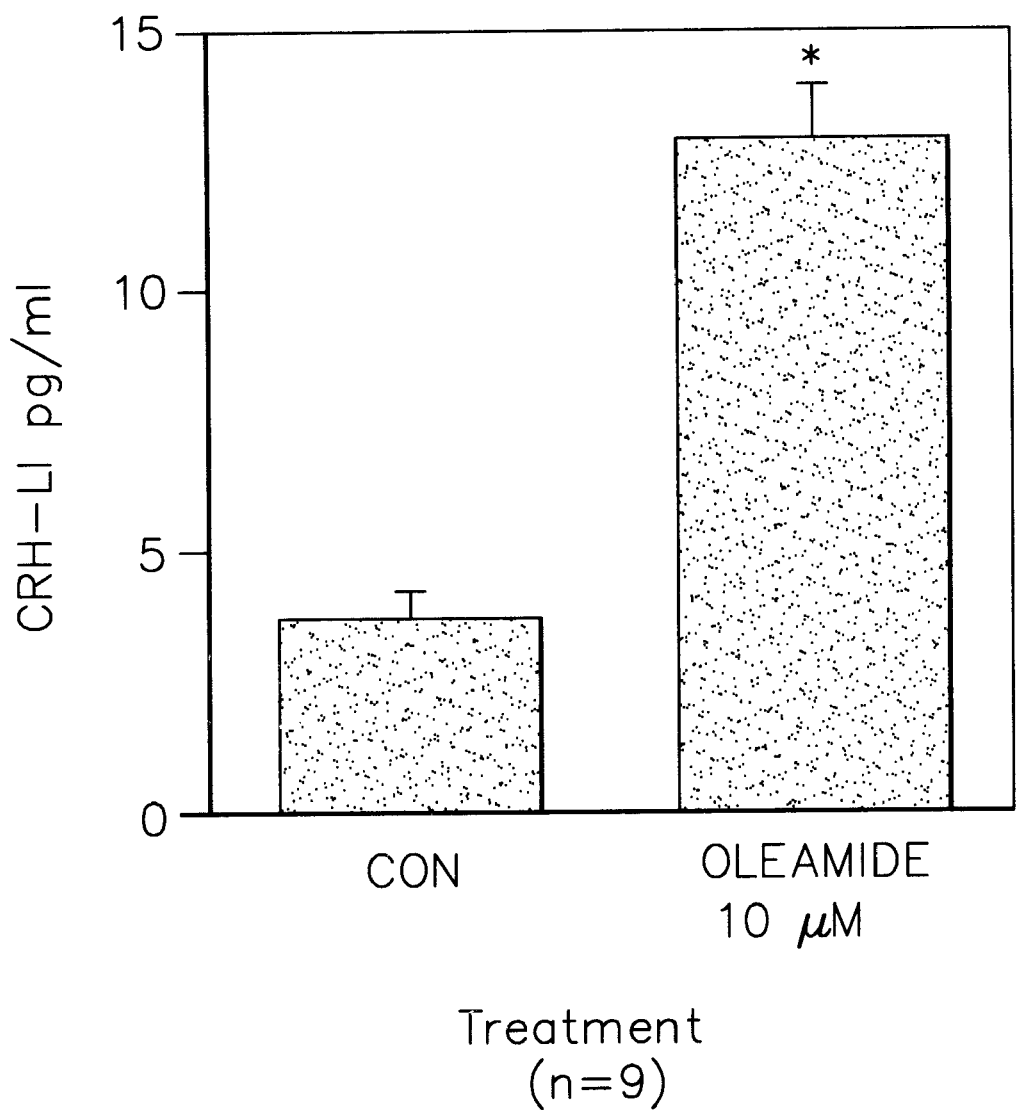
FIG. 2 shows the increase in immunoreactive CRH release from the cloned IVB cells after exposure to 10 $\mu$M oleamide.

Oleamide administration resulted in significant concentration-dependent increases in release of CRH from cloned hypothalamic IVB cells (see FIG. 2). Oleamide also increased CRH synthesis in these cells, as manifested by increased CRH mRNA (see Northern Blots in FIG. 1, top, and pooled data in FIG. 1, bottom).

Figure Legends

CRH messenger RNA changes in immortalized cultures at concentrations of 0 mM to 10 mM oleamide following 20 hours of incubation. FIG. 1, top, depicts a representative autoradiogram of the CRH Northern blots at 18 hours with two concentrations of oleamide. Also depicted is a representative Northern Blot of the 28 S ribosomal band (28S) in which no significant changes were detected. FIG. 1, bottom, depicts the densitometric values of CRH mRNA levels resulting from each concentration at various time points normalized to values obtained from 28S. FIG. 2 shows the significant increase in immunoreactive CRH (CRH-LI) release from the cloned IVB cells after exposure to 10 µM oleamide, compared with exposure to vehicle. Bars represent mean±standard error of the mean (n=3 for mRNA and 9 for CRH-LI). Statistical significance for each concentration in comparison to control, as determined by ANOVA and student's t test with Bonferroni's correction, is represented by * for P<0.05. Each figure is the result of pooled data from 3 independent experiments. Each independent experiment was performed on a different passage of cells.

Elevated Plus Maze

Methods for elevated plus maze testing were as follows: Based on Lister (1987), a 2 feet-4 arm radial maze consisting of 2 opposing enclosed arms (30 cm high×30 cm long×5 cm wide) and 2 opposing exposed arms (30 cm×5 cm) was constructed and was elevated on a pedestal 30 cm above the surface of a table and situated in the center of a dimly lit room. Testing was conducted in a quiet, dedicated room that was dimmed to provide 22 to 350 lux of illumination on the exposed arms of the maze and less than 1 lux within the enclosed arms. Animals were placed facing towards the enclosed arm in the center of the plus maze. Testing took place for 5 minutes based on Heinrichs et al. (1992 , 1994). We assessed time in open arms and closed arms, total number of entries and rearings, based on Windle et al. (1997). All observers were blind to treatment to remove any investigator bias.

Results

Results from elevated plus maze testing for a 2 mg dose given to rats (n=10 per group) weighing approximately 250 g show an overall increase in exploratory behavior. Rearings increased at 5 and 10 min of testing; P=0.002 and 0.01 respectively [means: 5 min–8.2 (control) vs 17.2 (oleamide); 10 min–15 (control) vs 24 (oleamide)]. The total number of entries to both open and closed arm were significantly increased (approximately doubled) after administration of oleamide relative to vehicle (P=0.0241).

CONCLUSION

Our discovery that oleamide increases CRH mRNA and stimulates secretion of CRH from cloned hypothalamic cells and also increases exploratory behavior on the elevated plus maze, in combination with the earlier findings that CSF CRH levels are low in many patients with anxious major depression (Geracioti et al., 1992 and 1997), and that brain CRH mRNA increases after use of the antidepressant treatment electroconvulsive therapy (Brady et al 1994), form the basis for administering oleamide or an inhibitor of its hydrolysis (including those oleamide hydrolase inhibitors that are disclosed in U.S. Pat. No. 5,856,537) to patients with depression and/or anxiety disorders. Conversely, the hyperactivity of CNS CRH in other patients with major depression (Nemeroff et al 1984) and some forms of anxiety disorder, such as post-traumatic stress disorder (Baker et al 1999), form the basis for the use of oleamide antagonists in these conditions. In this regard, several antidepressant agents cause reductions in CNS CRH concentrations or synthesis (Brady et al., 1991 & 1992).

What is claimed is:

1. A method of treating mood and anxiety disorders by administering to an individual in need of such treatment a safe and effective dose of oleamide, an oleamide analog, an inhibitor of oleamide degradation or clearance, or an oleamide antagonist.

2. The method of claim 1 comprising the administration of oleamide or an oleamide analog.

3. The method of claim 2 wherein the oleamide analog is selected from $C_{12}$–$C_{24}$ saturated fatty acid amides.

4. The method of claim 1 comprising the administration of an oleamide antagonist.

5. The method of claim 2 wherein said oleamide or oleamide analog is administered orally, transdermally, subcutaneously, parenterally, intramuscularly, intravenously, intraperitoneally or via inhalation.

6. The method of claim 4 wherein said oleamide antagonist is administered orally, transdermally, subcutaneously, parenterally, intramuscularly, intravenously, intraperitoneally or via inhalation.

7. The method of claim 1 wherein the targeted mood and anxiety disorders exist either independently or as comorbid conditions.

8. The method of claim 5 wherein said mood disorders being treated include depression, major depression, melancholic depression, atypical depression, minor depression, seasonal depression, bipolar affective disorder, dysthymia, menstrual cycle-related dysphoria, chronic fatigue syndrome, depression associated with somatoform disorders, fibromyalgia, and treatment-resistant depression.

9. The method of claim 5 wherein said anxiety disorders being treated include post-traumatic stress disorder (PTSD), generalized anxiety disorder, panic disorder with and without agoraphobia, social phobia, tics, tourette's syndrome, and obsessive-compulsive disorder.

10. The method of claim 1 wherein the oleamide, oleamide analog, inhibitor of oleamide degradation, or oleamide antagonist is administered in combination with a conventional antidepressant or anxiolytic treatment.

11. The method of claim 1 wherein the oleamide, oleamide analog, inhibitor of oleamide degeneration or oleamide antagonist is administered at a dose of rom about 0.01 to about 15 mg/kg.

12. The method of claim 11 comprising the administration of oleamide or a saturated $C_{16}$–$C_{20}$ fatty acid amide.

13. The method of claim 12 comprising the administration of oleamide.

\* \* \* \* \*